United States Patent
Schroeder

(10) Patent No.: US 10,617,476 B2
(45) Date of Patent: Apr. 14, 2020

(54) AUTOMATIC INSTRUMENT DETECTION AND IDENTIFICATION FOR A SURGICAL NAVIGATION SYSTEM

(71) Applicant: General Electric Company, Schnectady, NY (US)

(72) Inventor: Tobias Schroeder, Boston, MA (US)

(73) Assignee: General Electric Company, Schenectady, NY (US)

(*) Notice: Subject to any disclaimer, the term of this patent is extended or adjusted under 35 U.S.C. 154(b) by 1030 days.

(21) Appl. No.: 15/134,092

(22) Filed: Apr. 20, 2016

(65) Prior Publication Data

US 2016/0228201 A1 Aug. 11, 2016

Related U.S. Application Data

(62) Division of application No. 13/442,634, filed on Apr. 9, 2012, now abandoned.

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/062* (2013.01); *G01B 7/00* (2013.01); *G01B 7/02* (2013.01); *G01B 21/02* (2013.01); *G01B 21/047* (2013.01); *A61B 2017/00482* (2013.01); *A61B 2034/2046* (2016.02); *A61B 2034/2051* (2016.02); *A61B 2034/2053* (2016.02); *A61B 2034/2065* (2016.02); *A61B 2034/254* (2016.02)

(58) Field of Classification Search
CPC .. A61B 2017/00482; A61B 2034/2051; A61B 34/20; A61B 5/062; A61B 2034/254; A61B 2034/2065; A61B 2034/2053; A61B 2034/2046; G01B 7/02; G01B 7/00; G01B 21/047; G01B 21/02
See application file for complete search history.

(56) References Cited

U.S. PATENT DOCUMENTS 6,428,547 B1 8/2002 Vilsmeier et al.
7,840,253 B2 11/2010 Tremblay et al.
(Continued)

*Primary Examiner* — Amanda Lauritzen Moher

(57) ABSTRACT

A detection and identification system of instruments for use with a surgical navigation system is described. The navigation system contains an instrument assembly containing a coil (of a receiver) having an interior space, an instrument configured to be removably coupled to the coil, and a prong affixed to the instrument and configured to be at least partially disposed within the interior space of the coil when the instrument is coupled to the coil, where the prong has a length corresponding to physical dimensions of the instrument. The navigation system can also contain a transmitter located within the body of a patient. The navigation system can identify interchangeable instruments by providing one or more instruments each having a prong of a length corresponding to the physical dimensions of the instrument, providing a receiver configured to be coupled to the one or more instruments, the receiver having a coil with a depth; and identifying if the one or more instruments is coupled to the receiver based on the length of the prong when the one or more instruments is coupled to the receiver.

5 Claims, 4 Drawing Sheets

(51) Int. Cl.
  *G01B 21/02* (2006.01)
  *G01B 21/04* (2006.01)
  *G01B 7/00* (2006.01)
  *G01B 7/02* (2006.01)
  *A61B 17/00* (2006.01)
  *A61B 34/00* (2016.01)

(56) References Cited

U.S. PATENT DOCUMENTS

| | | | |
|---|---|---|---|
| 2003/0073972 A1* | 4/2003 | Rosenman | A61B 17/3468 |
| | | | 604/502 |
| 2004/0068299 A1* | 4/2004 | Laske | A61M 25/0082 |
| | | | 607/3 |
| 2004/0220471 A1 | 11/2004 | Schwartz | |
| 2006/0200025 A1 | 9/2006 | Elliott et al. | |
| 2008/0021532 A1* | 1/2008 | Kveen | A61N 1/0573 |
| | | | 607/115 |
| 2009/0069671 A1* | 3/2009 | Anderson | A61B 5/06 |
| | | | 600/424 |
| 2013/0282007 A1* | 10/2013 | Chong | A61B 5/0422 |
| | | | 606/41 |

* cited by examiner

AUTOMATIC INSTRUMENT DETECTION AND IDENTIFICATION FOR A SURGICAL NAVIGATION SYSTEM

CROSS-REFERENCE TO RELATED APPLICATIONS

The present application is a divisional application of and claims priority to U.S. patent application Ser. No. 13/442,634, filed on Apr. 9, 2012, the entirety of which is incorporated herein by reference.

BACKGROUND

This disclosure relates generally to identifying interchangeable instruments, and more particularly to automatically detecting and identifying interchangeable instruments for use in with an electromagnetic surgical navigation and/or tracking system.

Electromagnetic tracking systems have been used in various industries and applications to provide position and orientation information relating to instruments or objects. For example, electromagnetic tracking systems may be useful in aviation applications, motion sensing applications, retail applications, and medical applications. In medical applications, electromagnetic tracking systems have been used to provide an operator (e.g., a physician, surgeon, or other medical practitioner) with information to assist in the precise and rapid positioning and orientation of an instrument (such as a medical device, implant, tool, or other implement) located in or near a patient's body during image-guided surgery. The electromagnetic tracking system provides position and orientation information for an instrument with respect to the patient's anatomy or to a reference coordinate system. The electromagnetic tracking system provides intraoperative tracking of the precise location of the instrument in relation to multidimensional images of a patient's anatomy. As the instrument is positioned within or with respect to the patient's anatomy, the displayed image is continuously updated and tracked to reflect the real-time position and orientation of the instrument being used.

The known physical size and shape of the instrument can be used to calculate the location and orientation of each portion of the instrument, which is then used, in turn in generating and displaying the real time position of each portion of the instrument. The combination of the image and the representation of the tracked instrument in real time provide position and orientation information that allows a medical practitioner to manipulate the instrument to a desired location with an accurate position and orientation and display that location along with other reference structures or anatomy.

When different instruments are used with electromagnetic tracking systems, the system must be calibrated to the known physical size and shape of the particular instrument being used so it will be properly be represented on the display. Hall-effect sensors in a receiver and permanent magnets organized in a particular pattern in the instruments have been used in the past to detect and identify the different instruments being used during surgical procedures.

SUMMARY

This application relates generally to an automatic detection and identification system of instruments being used with a surgical navigation system. The surgical navigation system includes an instrument assembly containing a coil (of a receiver) having an interior space, an instrument configured to be removably coupled to the coil, and a prong affixed to the instrument and configured to be at least partially disposed within the interior space of the coil when the instrument is coupled to the coil, where the prong has a length corresponding to physical dimensions of the instrument. The navigation system can also contain a transmitter located within the body of a patient. The navigation system can identify interchangeable instruments by providing one or more instruments each having a prong of a length corresponding to the physical dimensions of the instrument, providing a receiver configured to be coupled to the one or more instruments, the receiver having a coil with a depth; and identifying if the one or more instruments is coupled to the receiver based on the length of the prong when the one or more instruments is coupled to the receiver.

BRIEF DESCRIPTION OF THE DRAWINGS

The following description can be better understood in light of the drawings, in which.

Figure 1:
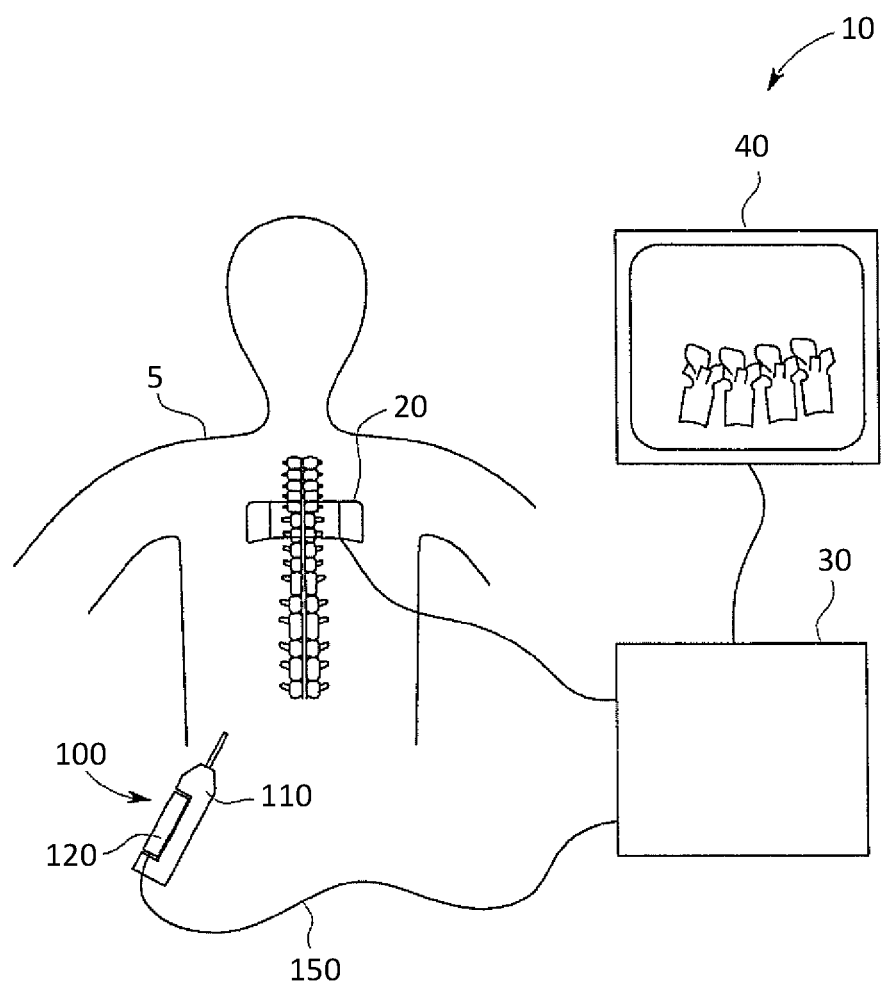
FIG. 1 shows a schematic diagram of an embodiment of an exemplary electromagnetic surgical navigation system.
Figure 2:
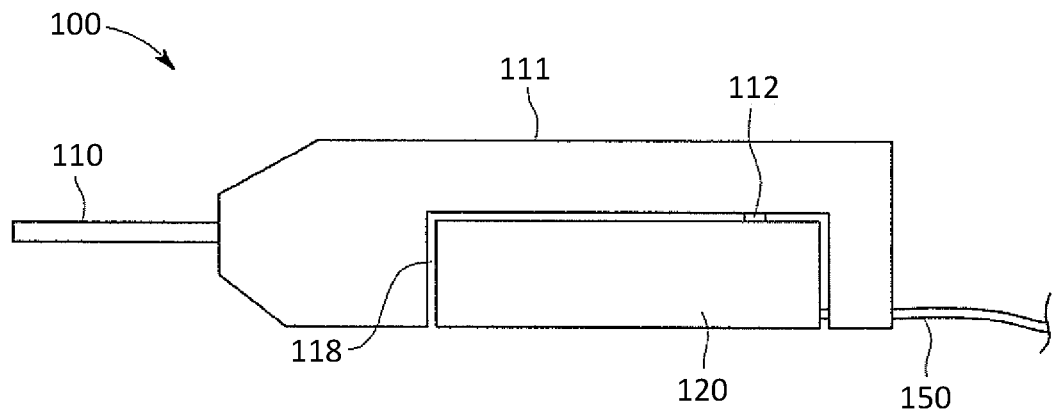
FIG. 2 shows a side perspective diagram of an embodiment of an exemplary instrument handle with an electromagnetic sensor pack coupled therein.

The drawings illustrate specific aspects of the described components, systems and methods for automatic instrument detection and identification for use with a surgical navigation system. Together with the following description, the drawings demonstrate and explain the principles of the structures, methods, and principles described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described components, systems and methods.

DETAILED DESCRIPTION

The following description supplies specific details in order to provide a thorough understanding. Nevertheless, the skilled artisan will understand that the described systems and methods for identifying interchangeable instruments can be implemented and used without employing these specific details. Indeed, the described systems and methods for identifying interchangeable instruments can be placed into practice by modifying the described systems and methods and can be used in conjunction with any other apparatus and techniques conventionally used in the industry. For example, while the description below focuses automatically identifying different instruments used with surgical navigation systems, the methods and systems for automatically identifying instruments may be used in other systems requiring interchangeable instruments.

In addition, as the terms on, disposed on, attached to, connected to, or coupled to, etc. are used herein, one object (e.g., a material, element, structure, member, etc.) can be on, disposed on, attached to, connected to, or coupled to another object—regardless of whether the one object is directly on, attached, connected, or coupled to the other object or whether there are one or more intervening objects between the one object and the other object. Also, directions (e.g., on top of, below, above, top, bottom, side, up, down, under, over, upper, lower, lateral, orbital, horizontal, etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements. Furthermore, as used herein, the terms a, an, and one may each be interchangeable with the terms at least one and one or more.

FIG. 1 shows some embodiments of an electromagnetic surgical navigation system 10. The electromagnetic surgical navigation system 10 may comprise an electromagnetic field generator or transmitter 20 that is fixed to a particular anatomy of interest (i.e., a part of a patient 5); an electromagnetic receiver sensor pack 120 coupled to an instrument 110 making up an instrument assembly 100; a navigation tracker assembly 30 that preferable includes a sensor detection unit or tracker (not shown), a patient-to-image registration unit (not shown) and an image processing and storage unit (not shown); and a display 40 for displaying images and the position and orientation of an instrument superimposed on the images. In an exemplary embodiment, the navigation tracker assembly 30 preferable includes a computer, processor and memory to calculate the position and orientation of the instrument and provide signals for display of the images and instrument. Signals from the transmitter 20 and receiver sensor pack 120 may be sent to the navigation tracker assembly 30 for processing. The transmitter 20 may include an array of one or more transmitter coils (not shown). The receiver sensor pack 120 may also include an array of one or more receiver coils (not shown) and an instrument detection coil 126 (shown in FIGS. 3-5). The navigation tracker assembly 30 may also include a power supply and electronic circuitry to energize the instrument detection coil 126, generate voltages and current to drive the one or more transmitter coils and measurement circuitry to measure the mutual inductances between transmitter and receiver coils.

For example, in some embodiments each of the receiver sensors 122 and the transmitters 20 may include coil assemblies with a trio of orthogonal and collocated coils that are arranged in particular positions and orientations to determine movements and positions of the coils assemblies relative to each other. Similarly, coil sizes and number of windings may differ between receiver and transmitter coil assemblies, as well as among the various coils in a coil architecture trio, as desired. In some embodiments, the navigation tracker assembly 30 may include physical dimensions of various instruments stored in memory, such as for the different instruments shown in FIGS. 3-5. The navigation tracker assembly 30 may further include capabilities to store the physical dimensions of new instruments or connectivity to other computers, networks, or databases where information to provide the physical dimensions of various instruments may be available, depending on the instrument 110 being used.

In order to determine the position and orientation of an instrument being used during surgery, an alternating current drive signal may be provided to each coil of the transmitter 20 to create an electromagnetic field around the transmitter. As mentioned, this generates an electromagnetic field that is emitted from each coil of the transmitter 20. The electromagnetic field generated by each coil in the transmitter 20 may induce a voltage in each coil of the receiver sensor 122. These voltages may be indicative of the mutual inductances between the coils of the transmitter 20 and the coils of the receiver sensors 122. These voltages and mutual inductances may be sent to the navigation tracker assembly 30 for processing. The navigation tracker assembly 30 may use these measured voltages and mutual inductances to calculate the position and orientation of the instrument 110, including six degrees of freedom (x, y, and z measurements, as well as roll, pitch and yaw angles).

The calculated position and orientation of the instrument 110, along with the detection and identification of the instrument 110, known physical dimensions of the instrument 110, and the physical location and dimensions of the anatomy of the patient 5, may be used to calculate the position an orientation of the instrument 110 with respect to the anatomy of the patient 5. The calculated positions and orientations may then be displayed on display 40 for use by a physician, surgeon, or other medical practitioner while performing a surgical procedure on the patient 5.

FIGS. 2-5 illustrate some embodiments of instrument assemblies 100 including an instrument 110 coupled to an instrument handle 111. The instrument handle 111 including an opening 118 for receiving a receiver sensor pack 120 therein. The receiver sensor pack 120 may be electronically coupled to navigation tracker assembly 30 through a wired connection illustrated as cable 150.

The instrument handle 111 may include an opening 118 configured to accommodate the receiver sensor pack 120 and provide some structure to assist in holding the receiver sensor pack 120 in place with the instrument 110.

The instrument handle 111 may be formed of any suitable material for use as a tool, medical instrument, etc. For example, when used as a medical instrument, the instrument handle 111 may comprise any material suitable for use as a medical instrument, including plastics, metals, or combinations thereof.

Figure 3:
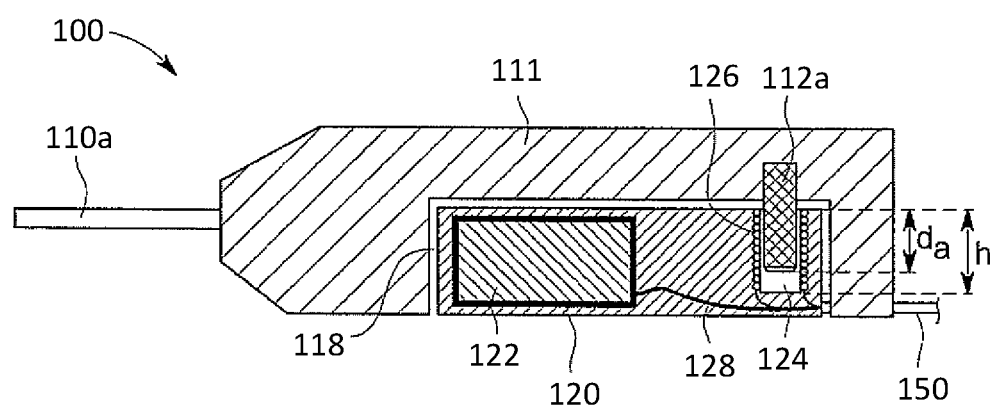
FIGS. 3-5 show cross-sectional diagrams of embodiments of exemplary instrument handles with an electromagnetic sensor packs coupled therein.
Figure 4:
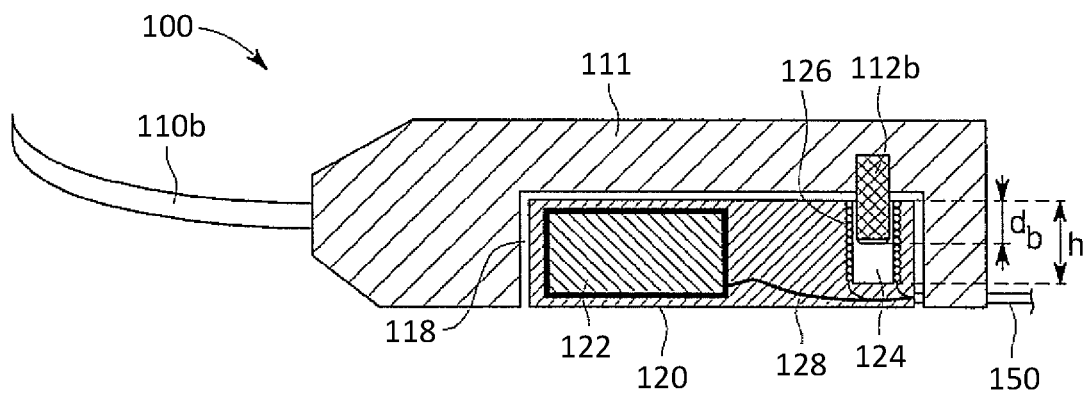
Figure 5:
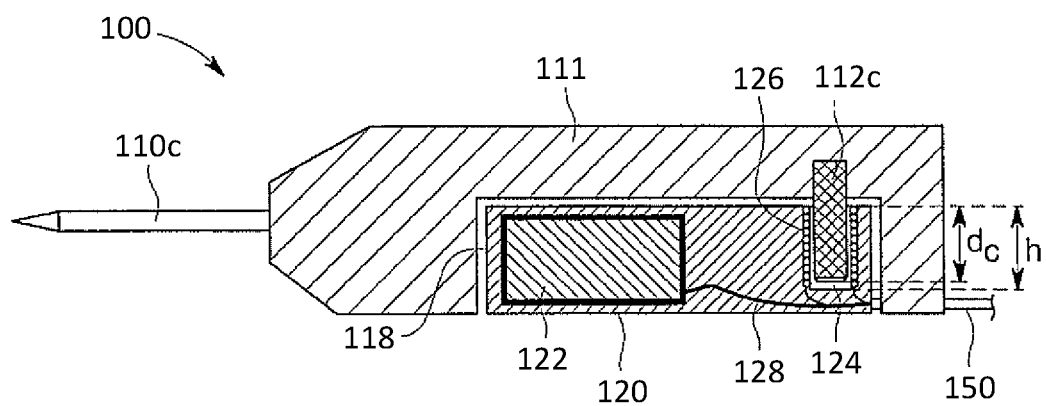

In FIGS. 3-5 different instruments 110a-110c are shown for the purpose of representing examples of interchangeable instruments 110 and do not necessarily represent any particular instrument that may be used with the electromagnetic surgical navigation system 10. As such, instrument 110 may be coupled to an instrument handle 111 that may be coupled with a receiver sensor pack 120. The specific instruments 110a, 110b, and 110c are described in detail below.

The instrument handle 111 may also include a prong 112. The prong 112 may be formed of any material sufficient to affect the impedance of the coil 126 as described in detail below. For example, in some embodiments the prong 112 may be formed from a high-permeability material, a ferromagnetic material, a medical-grade stainless steel, or any other suitable material that would affect the impedance of the coil 126 when the prong 112 is inserted into the open core 124 of coil 126.

The prong 112 may have a length selected based on the type of instrument 110. In some embodiments, the prong may have a length ranging from about 2 mm to about 10 mm. For example, as shown in FIG. 3, the instrument contains a prong 112a having an exposed prong length of $d_a$. The prong length (i.e., $d_a$ in FIG. 3) may cooperate with the coil 126 to provide detection and identification to navigation tracker assembly 30 that the instrument 110 is of a particular type. The types, including size and shape of various instruments may be stored into memory and accessible by navigation tracker assembly 30 for use in tracking the instrument 110. Thus, the particular type of instrument (i.e., 110a) may be determined by the size or length of the prong (i.e., 112a). Similarly, the prong length $d_b$ of the prong 112b may correspond to the instrument 110b type in FIG. 4 and the prong length $d_c$ of the prong 112c may correspond to the instrument 110c type in FIG. 5.

The prong 112 may be contained in the instrument handle 111 such that it is securely attached to the instrument handle 111. In some embodiments, the prong 112 may be co-molded with the instrument handle 111 as the instrument handle 111 is formed. In such embodiments, the prong 112 may contain a protrusion that helps to secure the prong 112 into the instrument handle 111 without allowing the prong 112 to fall out of or otherwise move with respect to the instrument handle 111. In other embodiments, the prong 112 may be bonded to the instrument handle 111 with adhesive, press-fit, or other technique to couple the prong 112 to the instrument handle 111. In yet other embodiments, the prong 112 may be attached or connected to the instrument handle 111 by screwing it into a threaded hole.

The receiver sensor pack 120 may include a receiver sensor 122 and an instrument detection coil 126 having an open core 124, as shown in FIGS. 3-5. In some configurations, the receiver sensor pack 120 may be formed using a thermoplastic resin encapsulating the various interior components of the receiver sensor pack 120. In other configurations, the receiver sensor pack 120 may formed of multiple components such that the interior is accessible for assembly of the receiver sensor pack 120, and, in some instances, for repair, recalibration, or replacement of various components of the receiver sensor pack 120.

The receiver sensor pack 120 contains a receiver sensor 122 which may contain one or more coils (as described herein) and may work in conjunction with the transmitter 20 and the navigation tracker assembly 30 (as described herein) to help establish a position and orientation of instrument 110 relative to patient anatomy. The receiver sensor 122 and the instrument detection coil 126 may be electrically connected to the navigation tracker assembly 30 through wires or conductors 128, which may be included within cable 150 that is coupled to the navigation tracker assembly 130.

The receiver sensor pack 120 also contains a instrument detection coil 126 having an open core 124. The prong 112 from the instrument handle 111 may then be inserted into the open core 124 so that the coil 126 surrounds the prong 112. The receiver sensor pack 120 and the instrument handle 111 may be connected to each other by any suitable connection elements or techniques to form the instrument assembly 100. For example, the receiver sensor pack 120 and the instrument handle 111 may be coupled together using detents, latches, access doors, straps, pins, etc.

In some embodiments, the instrument detection coil 126 may be multiple coils. The impedance of each of the multiple coils may be measured separately or collectively to achieve increased sensitivity to different lengths of the prong 112. Each of the multiple coils may have similar or different configurations, yielding varying impedance response profiles, which can be used to further differentiate different prongs. Multiple coils may provide for a response that resembles a digital response to a particular prong length. In some embodiments, the configuration of the coil 126 used in the receiver sensor pack 120 may be selected for sensitivity. For example, the impedance of coil 126 when the prong 112 is positioned within the open core 124 may be determined in order to indicate to the navigation tracker assembly 30 the specific type of instrument 110 attached to receiver sensor pack 120. As described herein, different lengths of prongs 112 may affect the measured impedance of coil 126.

In the illustrated embodiments, a coil having a particular number of windings of a particular thickness and physical properties may be selected such that when different lengths of prongs are inserted into the coil, the coil inductance changes depending on the length of the prong. As such, different length prongs provide different inductances, which correspond to coil impedance. The inductance can be measured, which can indicate the length of the prong in the coil. The length of the prong may then be used to identify the specific type of instrument being used.

The following example demonstrates how the coil impedance and inductance may be used to determine prong length to identify a particular type of instrument 110. The coil impedance may be determined using formula (I):

$$Z_{COIL} = R_{COIL} + jwL_{COIL} \quad (I)$$

where $Z_{COIL}$ is the measured voltage/measured current, $R_{COIL}$ is the DC resistance of the coil, $L_{COIL}$ is the coil inductance, j is the imaginary unit with the property j*j equal to −1, and w is the angular frequency of the driving voltage and is equal to $2\pi f$, where f is the driver voltage frequency.

Prior to attaching the receiver sensor pack 120 into the opening 118 in the instrument handle 111, $L_{COIL}$ may be measured as that of an air-core solenoidal coil. It can be calculated according to formula (II):

$$L_{COIL} = K(h) mu_0 N^2 A/h \quad (II)$$

where K(h) is the Nagaoka coefficient for coil length h, $mu_0$ is permeability of free space, N is the number of coil turns, and A is the coil cross sectional area. When the instrument 110 is coupled to the receiver sensor pack 120, the prong 112 enters the coil 126 by an instrument-specific distance d (such as $d_a$, $d_b$, $d_c$, as described herein and shown in FIGS. 3-5). Since the relative permeability of the prong material (mu) is greater than that of air, the coil inductance increases. As a result, the phase and magnitude of $Z_{COIL}$ changes. For an attached instrument, the coil inductance can be approximated using formula (III):

$$L_{COIL} = K(h-d) mu_0 [N[h-d]/h]^2 A/[h-d] + mu_{prong} F_L mu_0 [Nd/h]^2 A/d \quad (III)$$

which can be simplified to the formula (IV):

$$L_{COIL} = K(h-d) mu_0 N^2 A[h-d]/h^2 + mu_{prong} F_L mu_0 N^2 A d/h^2 \quad (IV)$$

and further simplified to the formula (V):

$$L_{COIL} = N^2 mu_0 A/h^2 [K(h-d)[h-d] + mu_{prong} F_L d] \quad (V)$$

where $mu_{prong}$ is the apparent relative permeability of the prong which depends on mu and the ratio of prong length and diameter, and $F_L$ is a factor that depends on the ratio of the prong length d and the pronghole depth h.

For example, in the embodiments shown in FIG. 4, the following values for an instrument with a 5 mm prong can be assumed: h=10 mm; coil core diameter=2 mm; N=500; mu=10 (stainless steel); $mu_{prong}$=5.5; $d_c$=5 mm; K(h)=0.91; K(h−d)=0.84; and $F_L$=0.72. For these values, $L_{COIL}$ prior to the instrument attachment is $L_{COIL}$=0.09 mH. After the instrument attachment, a value of $L_{COIL}$=0.24 mH is obtained. Assuming a coil wire thickness of 42 AWG, the DC resistance of approximately $R_{COIL}$=20 Ohms is obtained. If the coil is driven at a frequency of f=10 kHz, the value obtained prior to instrument attachment is $Z_{COIL}$=20 Ohms+j 5.6 Ohms. After attachment, the value obtained is $Z_{COIL}$=20 Ohms+j 14.9 Ohms. Thus, the magnitude of $Z_{COIL}$ increased by a factor of about 1.2, and the phase increases from about 15.6 degrees to about 36.7. Such an increase is well above the resolution of available current and voltage measurement technology.

Thus, the sensitivity of $Z_{COIL}$ may be affected by the prong length, d. The higher this sensitivity, the easier it may be to differentiate between prongs 112 of different lengths (such as the prongs 112a, 112b, and 112c of FIGS. 3-5). A higher sensitivity may indicate that more distinct instrument geometries (i.e. prong lengths) may be accommodated for a given coil depth. The sensitivity to the prong length d may be partially derived from $L_{COIL}$ as delta $L_{COIL}$/delta d=$N^2$ $mu_0$ $A/h^2$ [$mu_{prong}$ $F_L$-K(h-d)] which is 0.031 mH/mm. In terms of $Z_{COIL}$, a delta $Z_{COIL}$/delta d=jw 0.031 mH/mm is obtained. For a given frequency of 10 kHz, a delta $Z_{COIL}$/delta d=j 1.9 Ohms/mm is then arrived at. In summary, the sensitivity to various prong lengths d may be increased by increasing frequency, or choosing a prong material with higher permeability. And increasing sensitivity may allow for a wider range of prong lengths to more accurately identify different types of instruments and instruments configurations.

In some configurations, the instrument handle 111 may include more than one prong 112 and corresponding additional coils 126. The additional prongs 112 may be of the same or different lengths to further provide variation in the possible numbers and variety of instrument types that may be used with the receiver sensor pack 120. The additional prongs 112 may also function to releasably secure the receiver sensor pack 120 to the instrument handle 111. The instrument assembly 100 may also include other features (not shown) that hold the receiver sensor pack 120 to the instrument handle 111, such as detents, bias clips, bands, etc., or any feature that would removably hold receiver sensor pack 120 in contact with instrument 110.

Figure 6:
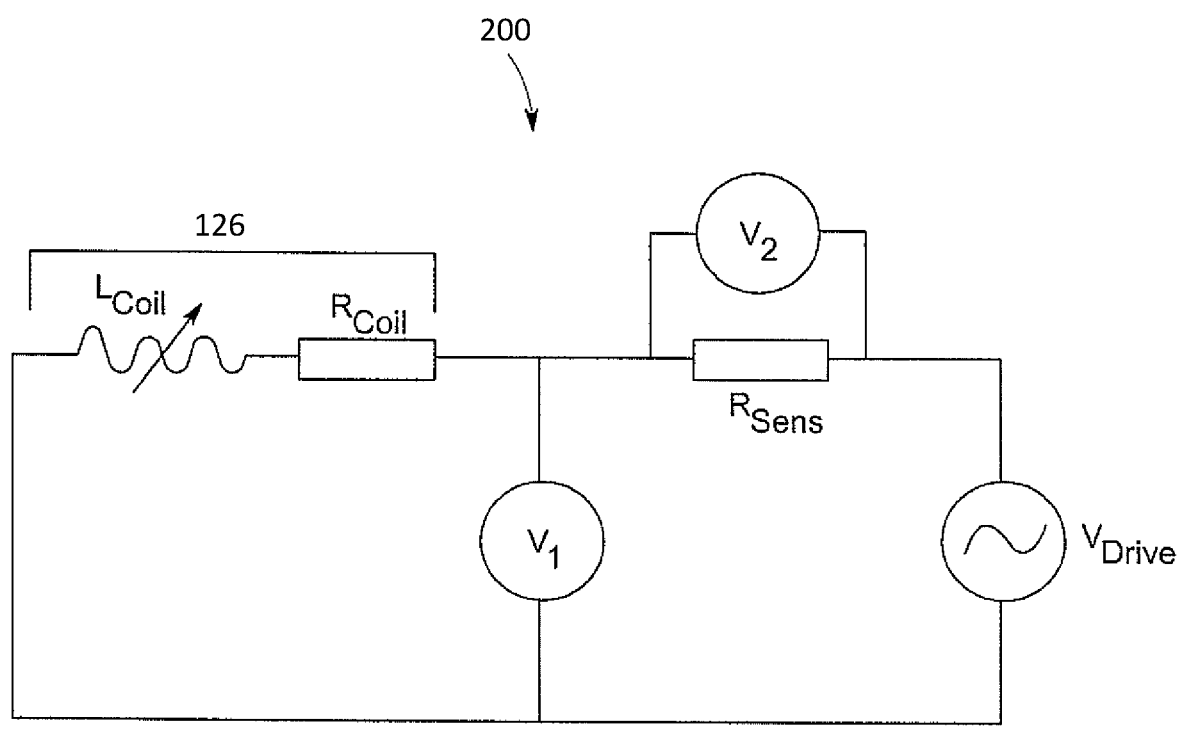
FIG. 6 shows a schematic representation of circuitry of an embodiment for detecting and identifying different instruments coupled to an electromagnetic sensor pack.

FIG. 6 shows a simplified circuit 200 that may operate to determine the inductance of the coil 126, $Z_{COIL}=R_{COIL}+jwL_{COIL}$ in some embodiments. $V_1$ may measure voltage across the coil 126, and $V_2$ may be used to determine coil current. The current signal may be measured by sensing the voltage across resistor $R_{Sens}$. The AC voltage $V_{Drive}$ may energize the coil 126.

Thus, by using different prong lengths, permeabilities, etc., instruments with various configurations and types can be easily and automatically identified by electromagnetic surgical navigation system 10. The prong and coil configurations described herein offer the advantage of a simple, reliable, and compact automatic instrument identification system for interchangeable instruments. Because of the robust design of a prong and encased coil, instruments and receivers may be used multiple times without significant risk of misidentification.

The automatic detection and identification system described herein may simplify the process for a user to use and calibrate instruments with a surgical navigation system. Conventionally, when different instruments are used with electromagnetic tracking systems, the system must be calibrated to the known physical size and shape of the particular instrument being used so it will be properly represented on the display. Hall-effect sensors in a receiver and permanent magnets organized in a particular pattern in the instruments have sometime been used to identify the different instruments. However, the Hall-effect sensors can require significant space requirements necessitating a large receiver, and the permanent magnets may become dislodged or otherwise unaligned such that proper identification of the instrument may be compromised.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

What is claimed is:

1. An instrument assembly for use in a surgical navigation system, the instrument assembly comprising:
    an instrument coupled to an instrument handle, the instrument handle including an opening for removably receiving a receiver sensor pack therein and a prong extending from the instrument handle into the opening a certain distance for detecting and identifying a type of instrument by the surgical navigation system;
    wherein the receiver sensor pack comprises a receiver sensor and an instrument detection coil having an open core;
    wherein the instrument is configured to be removably coupled to the receiver sensor pack;
    wherein the prong is configured to be at least partially disposed within the open core of the coil when the receiver sensor pack is removably coupled to the instrument handle and the prong having a length corresponding to a specific instrument type;
    wherein the instrument is a first instrument, the prong is a first prong, and further comprising:
    a second instrument configured to be removably coupled to the coil, the second instrument having physical dimensions differing from the physical dimensions of the first instrument;
    a second prong having a length corresponding to the physical dimensions of the second instrument; and
    wherein a processor is configured to identify the physical dimensions of the first instrument based on the length of the first prong and the physical dimensions of the second instrument based on the length of the second prong.

2. The instrument assembly of claim 1, wherein the instrument detection coil has an inductance that is affected when the prong is inserted into the open core of the coil.

3. The instrument assembly of claim 1, further comprising a navigation tracker assembly operably coupled to the receiver sensor pack and configured to determine the type of instrument when the receiver sensor pack is coupled to the instrument handle.

4. The assembly of claim 1, wherein the processor is configured to determine if the first instrument, the second instrument, or no instrument is coupled to the coil.

5. The assembly of claim 1, wherein the instrument assembly is configured to be connected to the transmitter of a surgical navigation system.

* * * * *